United States Patent [19]

Hyman

[11] 4,078,087

[45] Mar. 7, 1978

[54] METHOD AND COMPOSITION FOR TREATING TREES USING CERTAIN QUATERNARY AMMONIUM COMPOUNDS

[76] Inventor: Sam M. Hyman, 2216 LaFollette Ave., Manitowoc, Wis. 54220

[21] Appl. No.: 668,362

[22] Filed: Mar. 19, 1976

[51] Int. Cl.$^2$ .......................... A01N 9/20; A01N 9/24
[52] U.S. Cl. ........................................ 424/329; 71/121
[58] Field of Search ........................................ 424/329

[56] References Cited

U.S. PATENT DOCUMENTS

| | | | |
|---|---|---|---|
| 2,666,010 | 1/1954 | Stayner | 424/329 |
| 3,560,390 | 2/1971 | Gaines | 424/329 |

*Primary Examiner*—V. D. Turner
*Attorney, Agent, or Firm*—Wheeler, Morsell, House & Fuller

[57] ABSTRACT

A method and composition for fungicidal treatment of diseased trees such as those infected with Dutch elm disease or oak wilt involves the injection into the tree of a highly water soluble fungicide which is a blend of quaternary ammonium chloride compounds namely, dimethyl benzyl ammonium chloride, dimethyl ethylbenzyl ammonium chlorides and water. In strong concentrations, this composition is also usable as a sylvicide to kill trees for the purposes of clearing large sections of agricultural land in underdeveloped countries.

4 Claims, 3 Drawing Figures

METHOD AND COMPOSITION FOR TREATING TREES USING CERTAIN QUATERNARY AMMONIUM COMPOUNDS

BACKGROUND OF INVENTION

Various fungicides have been tested to control Dutch elm disease in the American elm. The most well-known of these fungicides is Dupont's "Benonyl" or "Benlate" which has been tested for many years. Various injection techniques have been employed with this fungicide and it has been found to have limited effectiveness in inhibiting fungal development in diseased trees. An injection technique commonly called the Mauget Trunk Injection System where a plurality of spaced independent capsules containing the "Benlate" are circumferentially arranged around the tree trunk with spiles or conduits extending into the trunk for gravity flow of the "Benlate" into the tree has been employed. Although some successful tests have resulted from use of "Benlate", the chemical does not appear to be effective for widespread use under variable conditions and where the crown infection is substantially greater than 5%. It is believed that "Benlate" does not have sufficient solubility in the tree to provide effective distribution of the fungicide throughout the tree.

SUMMARY OF INVENTION

The invention provides a highly soluble fungicide which has been successfully tested in the control of the fungi causing Dutch elm, oak wilt, wilt of maples, apple scab fungus and wet wood of elm. A blend of quaternary ammonium compounds with good water solubility and a good wetting action is readily transmitted and distributed in trees tested. Successful testing of this fungicide has involved the use of multiple holes approximately ⅜ inches in diameter, 1 inch deep and circumferentially spaced 5 to 6 inches apart around the trunk of the tree and at approximately 2 feet from the ground. The holes are located in the water transmitting zone of the tree which is the outer young sapwood or xylem, where water movement in trees occurs. A manifold line is employed and connected to the various holes by T-connectors. The fungicide is injected into the tree under pressure with a hand pumping device which includes a pump and a reservoir for the fungicide. In large trees several gallons of the fungicide are injected under pressure, in smaller trees 1 gallon has been found to be adequate to inhibit disease.

Further objects, advantages and features of the invention will become apparent from the following disclosure.

DESCRIPTION OF THE PREFERRED EMBODIMENT

Figure 1:
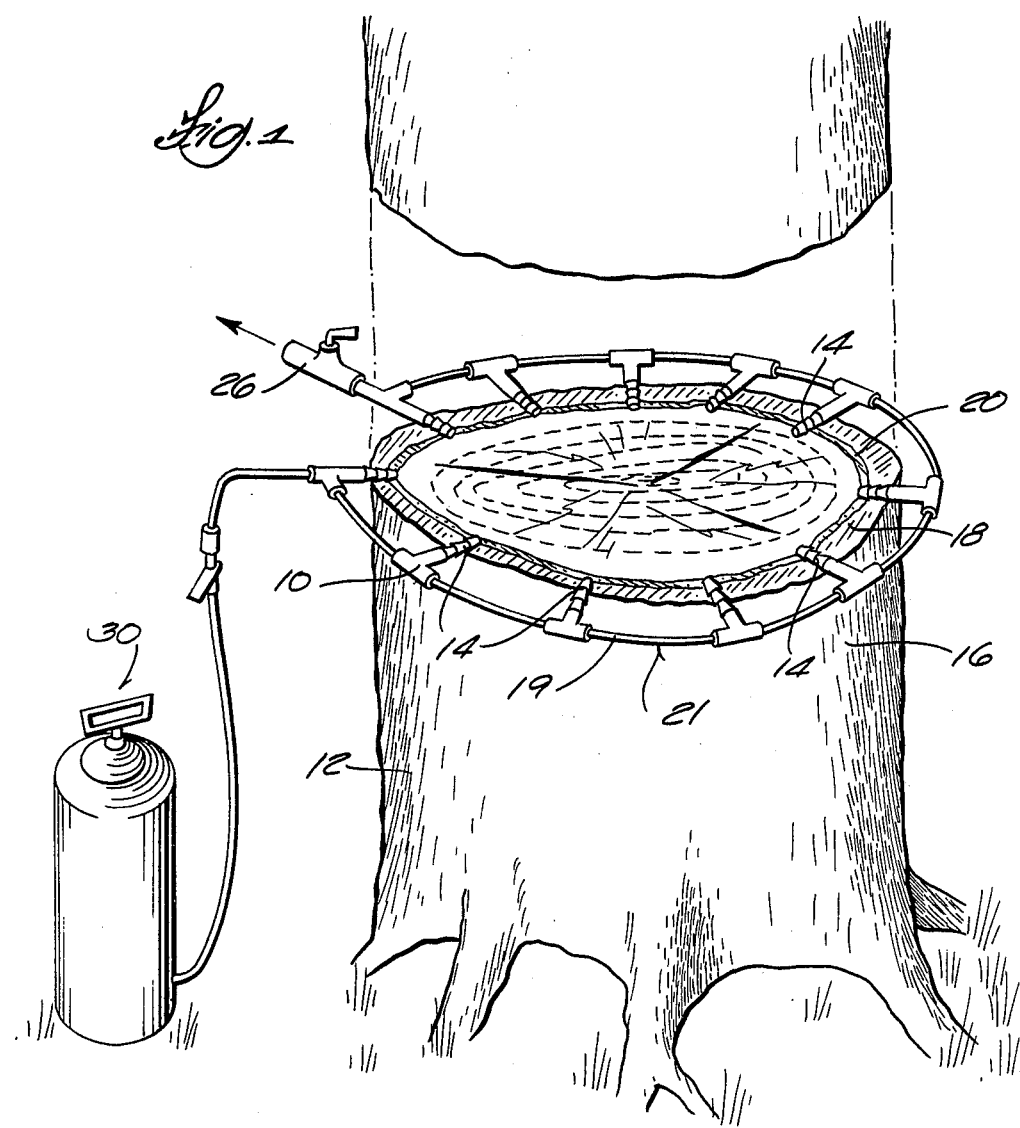
FIG. 1 is a schematic illustration of a method for inoculating a tree in accordance with the invention.

Although the disclosure hereof is detailed and exact to enable those skilled in the art to practice the invention, the physical embodiments herein disclosed merely exemplify the invention which may be practiced with other apparatus. The scope of the invention is defined in the claims appended hereto.

The figure shows apparatus for use in practicing the method of the invention. A series of T-connectors 10 are circumferentially arranged around the periphery of the tree trunk 12. The holes 14 in the tree can be approximately ⅜ to ½ inch in diameter and circumferentially spaced 5 to 6 inches apart. The injection holes are preferably located about 2 feet from the ground to facilitate manipulation of the apparatus. The injection holes can be approximately 1 inch deep and in any event, should penetrate outer bark 16, cambian layer 18, into the young sapwood or xylem 20 where water movement through the trunk to the branches occurs.

The T-connectors are connected by conduit sections 19 to form a manifold 21 which circumscribes the tree with the free end of the manifold 22 provided with an air valve 26 for release of air in the conduit 21 when the pumping of fungicide is initiated. Connected to the manifold 21 is a reservoir and pump assembly 30 which causes flow under pressure of the fungicide from the reservoir to the manifold and into the tree. The pressure reservoir assembly or pump desirably provides gauge pressure of 10 to 25 pounds per square inch to cause effective flow of the fungicide into the tree. The quantity of fungicide used depends on the circumference and height of the tree, as well as crown size. One to 3 gallons of the composition presently described has been found adequate to accomplish the intended results. The time required to pump the fungicide into a tree depends on the quantity employed and the rate of transpiration in the tree. On sunny, windy days it may take only 20 minutes and at other times up to 3 hours to administer the desired dosage.

It has been found that inoculation of a blend of quaternary ammonium compounds has provided outstanding results in combating Dutch Elm disease, Oak wilt disease and other diseases. The composition successfully tested includes by weight:

dimethyl benzyl ammonium chlorides n-alkyl (60% C14, 30% C16, 5% C12, 5% C18): 27% dimethyl ethylbenzyl ammonium chlorides n-alkyl (50% C12, 30% C14, 17% C16, 3% C18): 32% ethyl alcohol: 20%

The balance is made up of water. In addition, small quantities of 2-ethyl hexanol are added to stabilize the solution. Ninety ml of 2-ethyl hexanol for 414 lbs. of the other components was used in the tests subsequently described.

Prior to field testing, preliminary bioassay laboratory tests showed the above composition to be effective against oak wilt, dutch elm and wilt of maple. At concentrations of 1:10, 1:12, 1:15, 1:25, 1:30, 1:50, 1:60, 1:70, 1:80, 1:90, 1:100 and 1:110 (ratio of above chemical composition to water) growth of these fungi were inhibited by this fungicide.

The bioassay studies in the lab were conducted in triplicate with the above concentrations of the chemical in aqueous solutions. Then the bioassay absorbent discs 40 (FIG. 2) were dipped in the fungicidal solution of the various concentrations tested and placed in petri plates 42 at approximately 120° apart in a sterilized media (potatoe dextrose agar). The plates were inoculated in the middle with the actively growing *Ceratocystis ulmi* culture (Dutch Elm Disease Fungus) in order to test whether the chemical has any fungi static or fungi toxic effect on the fungus. The plates were incubated for 3 weeks in the incubator. Photographs were taken of all the plates after the incubation period.

Figure 2:
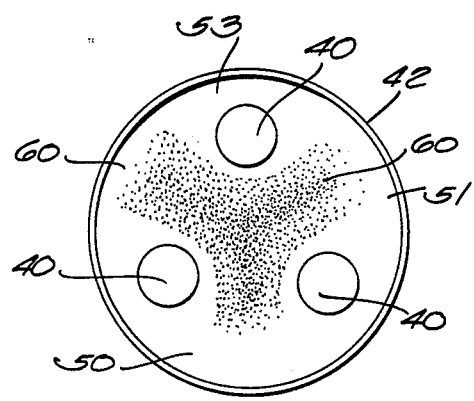
FIG. 2 is a diagrammatic plan view made from a photograph of a petri plate test of the fungicidal properties of the composition of the invention.

All the concentrations proved to be very effective against the Dutch Elm Disease fungus clearly showing the typical "zoning" as a clear indication that such concentrations could arrest or destroy the growth and multiplication of the fungus. FIG. 2 is a diagram made from a photograph of a petri plate, a concentration of one part concentrate to 60 parts water. FIG. 2 shows that growth of the Dutch Elm fungus was inhibited or retarded around the discs 40 treated with the fungicidal solution. The zones 50, 51, 53 are relatively free of growth.

Figure 3:
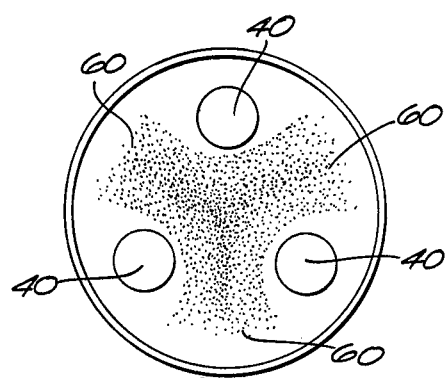
FIG. 3 is a view similar to FIG. 2.

FIG. 3 is a similar diagram in which the discs 40 were treated with the fungicide at a ratio of one part concentrate to 110 parts water. The lobes 60 of fungus growth in FIG. 3 are substantially greater in both width and radial extent than the growth with the stronger concentration of fungicide used in FIG. 2. Photographs were made of the various ratios of concentrate and water listed above.

The foregoing procedure was also conducted by inoculating petri plate media with *Ceratocystis fagacearum* (Oak Wilt Fungus). The results were comparable.

Subsequent to laboratory tests, 100 trees were injected with various of these concentrations. The oak were sensitive up to a ratio of 1 to 35 but above the ratio of 1 to 40 oaks showed no toxicity. Elm trees of 15 inches in diameter and above showed no toxicity above the range of 1 to 35.

After experimentation to determine toxicity ranges, healthy trees were subjected to two categories of testing: (a) trees were injected with the fungicide and after a week inoculated with the fungus; (b) trees were inoculated with a fungus first and then treated with the fungicide. With tests under (a) dosages between 1 to 40 and 1 to 70 prevented the development of the disease, showing clearly the effectiveness of the fungicide against the multiplication and spread of the fungi in the tree. Control trees which did not receive the fungicide died within 3 weeks while various percentages of the treated trees survided into the dormant winter stage. The following spring showed that fungus inoculated and fungicidal treated trees survived and leafed out along with healthy trees not involved in the test program.

The desirable results obtained with the fungicide of the invention are believed a result of the high water solubility which results in effective distribution in the trees. Trees treated with the fungicide have been tested to evaluate the distribution of the fungicide. Branches from trees inoculated with fungicide have been brought into the lab and sliced with the slices placed in a growth-enabling media instead of the discs 40. The reaction of the fungicide in the branch slices with the fungus in the plates could be observed. These test results compared favorably with the lab tests and thus, indicated that the fungicidal solution was readily transmitted through the tree to the branches, apparently due to the high water solubility of the fungicide. The fungicide described herein thus, was effective for treating the tree crown and upper limbs.

The examination of branches of trees treated with the fungicide indicates that the fungicide gives protection for approximately 1 year. Benlate breaks down in approximately 45 days and thus, does not give long term protection. Fungicidal activity of the chemical for at least 90 days is necessary.

Tests have also indicated concentrations of 1 to 10, 1 to 20 and 1 to 30 of the composition has a toxic effect on trees and is not toxic to man and wildlife and thus, is more desirable as a sylvicide than the highly toxic sodium arsenite which is commonly employed as a sylvicide in underdeveloped countries in large scale forest clearance.

I claim:

1. The method of treating trees to inhibit growth of destructive fungi comprising the step of injecting the water transmitting zone of the tree with a fungicidal solution consisting of a blend of water soluble quaternary ammonium chlorides and wherein the blend is a concentrate of dimethyl benzyl ammonium chlorides n-alkyl (60% C14, 30% C12, 5% C12, 5% C18) and dimethyl ethylbenzyl ammonium chlorides n-alkyl (50% C12, 30% C14, 17% C16, 3% C18) and the concentrate includes 20% by weight of ethyl alcohol, 27% dimethyl benzyl ammonium chlorides and 32% dimethyl ethylbenzyl ammonium chlorides and the concentrate is diluted with water in a ratio range by weight of between one part concentrate to 30 parts water and one part concentrate to 110 parts water and one to three gallons of the diluted concentrate are inoculated in each tree being treated once a year.

2. The method in accordance with claim 1 wherein said concentrate includes as a stabilizing agent 2-ethylhexanol in an amount sufficient to stabilize the solution.

3. The method in accordance with claim 1 wherein the trees are American Elm and wherein the concentrate is diluted with water in a ratio range by weight of between one part concentrate to 35 parts water and one part concentrate to 110 parts water.

4. The method in accordance with claim 1 wherein the trees are Oak and wherein the concentrate is diluted with water for fungicidal treatment in a ratio range by weight of one part concentrate to 40 parts water and one part concentrate to 110 parts water.

* * * * *